United States Patent [19]

Öhlin

[11] Patent Number: 4,746,491
[45] Date of Patent: May 24, 1988

[54] SERIAL DILUTION OF LIQUID SAMPLES

[75] Inventor: L. Erik Öhlin, Stocksund, Sweden

[73] Assignee: Swelab Instrument AB, Johanneshov, Sweden

[21] Appl. No.: 655,992

[22] Filed: Sep. 28, 1984

Related U.S. Application Data

[63] Continuation of Ser. No. 477,724, Mar. 22, 1983, abandoned.

[30] Foreign Application Priority Data

Mar. 27, 1982 [SE] Sweden .................... 8201791

[51] Int. Cl.⁴ .................. G01N 1/10; G01N 21/11; G01N 31/16; G01N 35/06
[52] U.S. Cl. ...................... 422/103; 422/63; 422/82; 422/100; 436/54; 436/179; 436/180; 137/625.42; 141/90; 73/863.73; 73/864.84
[58] Field of Search ............ 422/63, 81, 82, 100, 422/103; 436/179, 180, 49, 54, 74; 137/625.42; 141/86, 90; 73/863.71, 863.72, 863.73, 864.84

[56] References Cited

U.S. PATENT DOCUMENTS

| | | | |
|---|---|---|---|
| 3,223,123 | 12/1965 | Young | 73/863.72 |
| 3,291,347 | 12/1966 | Blades | 222/136 |
| 3,990,853 | 11/1976 | Godin | 23/259 |
| 4,148,859 | 4/1979 | Simpson et al. | 422/100 |
| 4,152,391 | 3/1984 | Cabrera | 422/103 |

FOREIGN PATENT DOCUMENTS 0116997 9/1979 Japan ....................... 422/103

Primary Examiner—Barry S. Richman
Assistant Examiner—Lynn Kummert
Attorney, Agent, or Firm—Hill, Van Santen, Steadman & Simpson

[57] ABSTRACT

An apparatus and method for serial dilution of liquid samples comprises a power-driven measuring valve having a rotatably mounted valve body provided with a single calibrated measuring passageway. During a dilution cycle the measuring passageway in different rotational positions of the valve body successively isolates a measured volume of a sample to be diluted and an equal volume of a first diluted solution of the sample which has been prepared by mixing the isolated undiluted volume of the sample with a measured volume of diluent. In a valve body position between said different rotational positions the measuring passageway is connected to form part of a rinsing flow system.

4 Claims, 2 Drawing Sheets

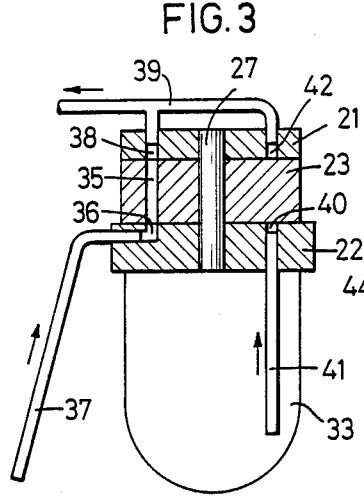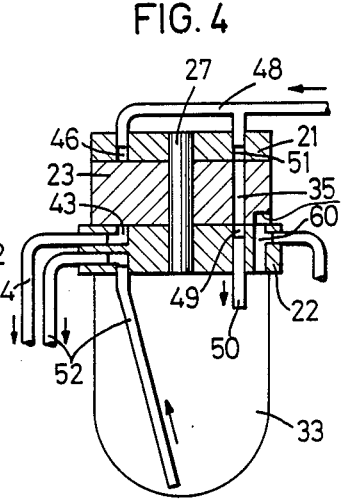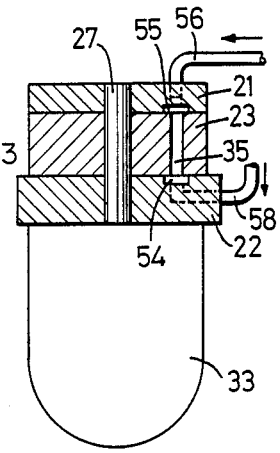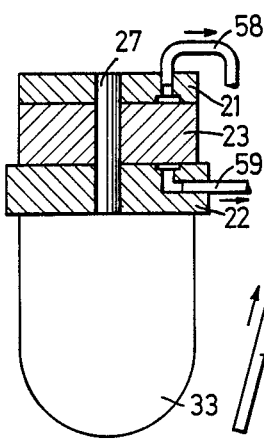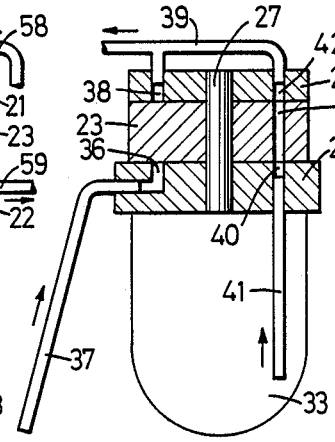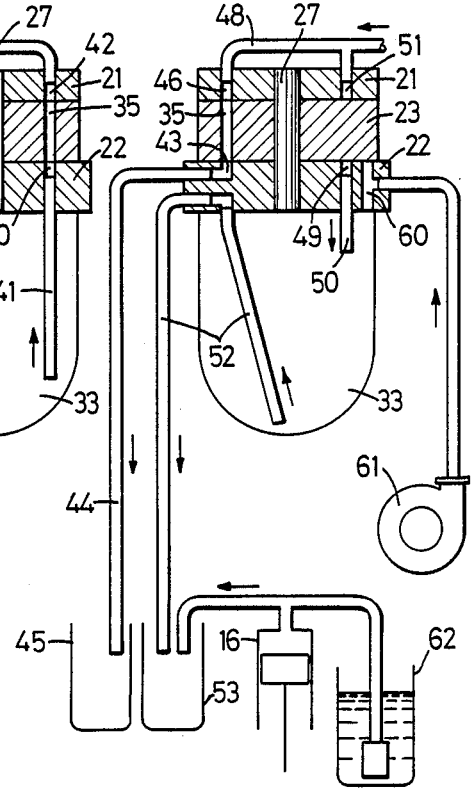

SERIAL DILUTION OF LIQUID SAMPLES

This application is a continuation of application Ser. No. 477,724, filed Mar. 22, 1983, now abandoned.

BACKGROUND OF THE INVENTION

1. Field of the invention

This invention relates to serial dilution of liquid samples and, more particularly, to a valve device for use in serial dilution of liquid samples and to a method of accomplishing such dilution.

2. Prior Art

Analysis of liquid samples is often carried out on two or more aliquots of a single sample diluted to different concentrations. Taking a blood sample, one aliquot may thus be diluted to form a first solution having a concentration of, say, 1:200, while another aliquot may be diluted to form a second solution having a concentration of, say, 1:50000. In such cases, where the concentrations differ by a factor of 100 or more, the preparation of the second solution normally has to be accomplished by serial dilution, that is, by further dilution of a portion of the first solution.

Automatic apparatus for performing serial dilution of liquid samples are known in the art, U.S. Pat. Nos. 3,291,347 and 3,990,853 showing exemplary embodiments.

In the prior art apparatus, a valve device comprising a housing and a valve body movably mounted in the housing is used to isolate measured volumes of the sample and the first solution, and to effect combination of such isolated volumes with measured volumes of diluent. The valve body is provided with a pair of through passageways of precise, known volumes. In one valve body position, the passageways are filled respectively with undiluted sample and the first solution, and in a second valve body position the volumes of the sample and the first solution are expelled from the passageways into different receiving vessels and mixed with measured volumes of diluent.

SUMMARY OF THE INVENTION

An object of the present invention is to provide a valve device for use in apparatus for serial dilution of liquid samples which permits accurate and rapid dilution of successive samples to be performed with a minimum of carry-over, that is, a minimum of contamination of samples with residues of previously diluted samples.

In accordance with one aspect of the invention, a valve device for use in apparatus for serial dilution of liquid samples comprises a valve housing, a valve body movably mounted in the housing, and a valve body actuator for moving the valve body relative to the housing. The housing includes various inlet and outlet ports for samples, diluent, and diluted sample solutions. A single calibrated passageway in the valve body can be selectively placed in register with several different combinations of the inlet and outlet ports, an important feature being that one and the same passageway is used to isolate successively, and with the valve body in different positions, a measured volume of undiluted liquid sample and an equal volume of a first solution of the liquid sample prepared by mixing the isolated volume of liquid sample with a measured volume of diluent. To minimize carry-over from the undiluted isolated volume of liquid sample to the isolated volume of the first solution, the valve device is provided with a rinse or wash liquid conveying system effective to rinse the passageway following the discharge therefrom of the undiluted volume of liquid sample and prior to the introduction of the first solution in the passageway.

Other objects, features and advantages of the invention will be evident from the following description of a preferred embodiment with reference to the accompanying drawings.

BRIEF DESCRIPTION OF THE DRAWINGS

FIGS. 3 to 8 are diagrammatic crosssectional views illustrating successive steps of a serial dilution cycle.

DESCRIPTION OF THE PREFERRED EMBODIMENT

Figure 1:
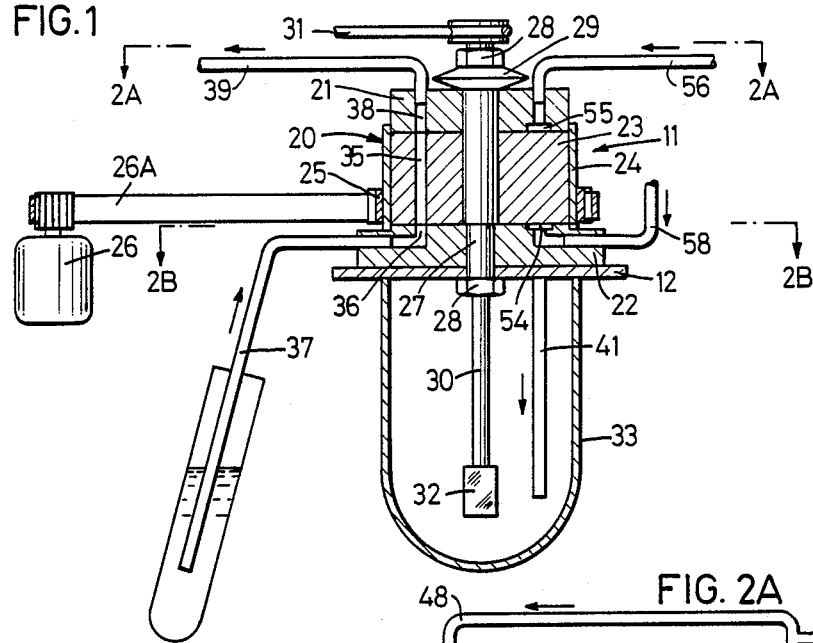
FIG. 1 is a diagrammatic cross-sectional view of a serial dilution apparatus comprising a valve device embodying the invention.

The serial dilution apparatus illustrated in the drawings comprises a valve device generally designated by 11 and supported by a frame, a portion of which is illustrated at 12. Connected to this valve device 11 are pump means in the form of a pair of peristaltic suction pumps 13 (FIG. 2A) and 14 (FIG. 2B) and a pair of proportioning piston pumps 15 (FIG. 2A) and 16 (FIG. 8).

The valve device 11 is a plane slide valve having a rotatably movable valve body 23. A stationary valve housing 20 comprises a top plate 21 and a bottom plate 22. Sandwiched between the top and bottom plates 21, 22 is the circular cylindrical valve body 23, the opposite plane and parallel faces of which sealingly engage the opposing faces or surfaces of the top and bottom plates 21, 22. A cylindrical sleeve 24 encircling and secured to the valve body 23 has its ends partially projecting over the top and bottom plates 21, 22. Secured to the sleeve 24 is a gear 25 which has a non-slip connection with an electrical valve body actuator motor 26 through a toothed belt 26A.

A central tubular shaft 27 rotatably guides valve body 23 relative to the top and bottom plates 21, 22. A pair of nuts 28 on the shaft 27 serve to clamp the top and bottom plates 21, 22 and the valve body 23 together through a compression spring 29. Extending through the tubular shaft 27 is a stirrer shaft 30, the upper end of which is connected to a stirrer motor (not shown, but may be combined with the valve body actuator motor) through a belt transmission 31. The lower end of the stirrer shaft 30 carries a stirring blade 32 and extends into a mixing vessel 33 sealingly engaging the frame 12.

A volumetrically calibrated passageway 35 extends axially through the valve body 23. Rotation of the valve body 23 will cause the passageway 35 to be blocked off at its ends or placed in communication with several pairs of axially registering ports in the top and bottom plates 21, 22 as is described below.

Opening into the upper face of the bottom plate 22 is an inlet port 36 in constant open communication with a sample aspirating tube 37. Opening into the lower face of the top plate 21 in register with the inlet port 36 is an outlet port 38 communicating through a conduit 39 with the suction pump 13.

Extending through the bottom plate 22 is an inlet port 40 (FIG. 3) which communicates with the bottom region of the mixing vessel 33 through an aspirating tube 41. An outlet port 42 opening into the lower face of the top plate 21 in register with the inlet port 40 communicates with the outlet port 38 through the conduit 39 and thus with the suction pump 13.

Opening into the upper face of the lower plate 22 is also an outlet port 43 (FIGS. 2B 4, 8) communicating through a discharge conduit 44 with a receiving vessel 45 for a second solution, that is, a liquid sample that has been twice diluted. In axial register with the outlet port 43, the lower surface of the upper plate 21 is provided with an inlet port 46 communicating with the proportioning pump 15 and a diluent container 17 through a conduit 48.

An outlet port 49 formed in the upper face of the bottom plate 22 opens through a short discharge conduit 50 into the mixing vessel 33. An inlet port 51, opening into the lower face of the top plate 21 in axial register with the outlet port 49, communicates with the inlet port 46 through the conduit 48 and thus with the pump 15.

Finally, a transfer conduit 52 extends from adjacent to the bottom portion of the mixing vessel to a receptacle 53.

Figure 2A:
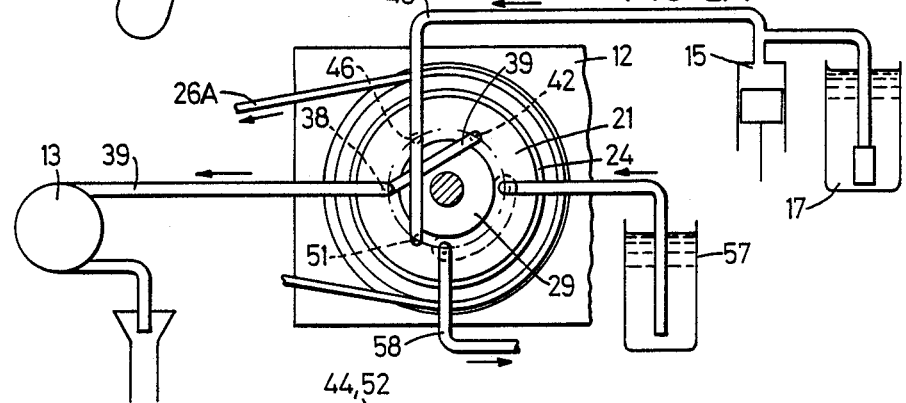
FIGS. 2A and 2B are diagrammatic cross-sectional views taken respectively on line 2A—2A and line 2B—2B of FIG. 1.
Figure 2B:
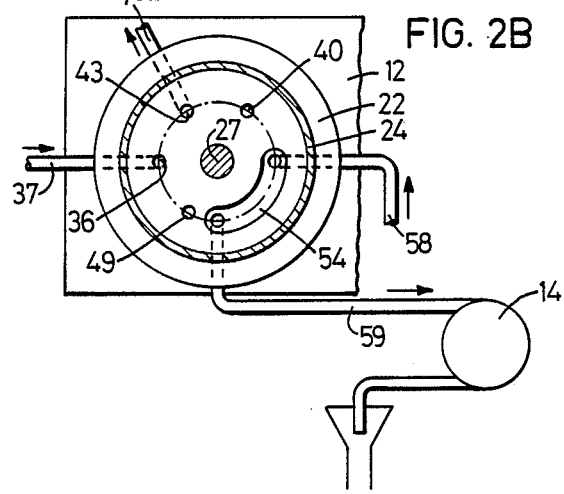

The locations of the above-mentioned inlet and outlet ports along the circular path along which the measuring passage 35 is moved during rotation of the valve body 35—such rotation is always counterclockwise, viewed from above as in FIGS. 2A and 2B—are shown in FIGS. 2A and 2B. FIGS. 1 and 2A, 2B also show that axially between the ports 40, 49 the one hand, and the ports 42, 51, on the other hand, a pair of recesses 54 and 55 is formed in the opposing faces of the top and bottom plates 21, 22. Both recesses, of which the recess 54 is formed in the upper face of the bottom plate 22 while the recess 55 is formed in the lower face of the top plate 21, are elongated in the circumferential direction and are slightly wider than the measuring passageway 35.

The end of the recess 55 which is closest to the ports 40, 42, that is, the "counterclockwise" end, is connected through an aspirating conduit 56 to a vessel 57 containing a suitable wash liquid, such as water to which a suitable detergent has been added. The other end, the "clockwise" end, is connected through a short transfer conduit 58 to the "counterclockwise" end of the recess 54, the "clockwise" end of which is connected to the peristaltic suction pump 14 through a conduit 59. Hence, with the pump 14 operating, wash liquid constantly flows first through the recess 55 and then through the recess 54, the flow taking place in the clockwise direction, that is, opposite to the direction of rotation of the valve body 23.

The recesses 54, 55 and/or the transfer conduit 58 are dimensioned such that when the measuring passageway 35 is in register with the recesses 54, 55, the major portion of the wash liquid transported by the pump 14 flows through the measuring passageway 35, while only a minor portion flows through the transfer conduit 58. Thus, with the measuring passageway 35 in register with the recesses 54, 55, the passageway short-circuits a substantial portion of the flow path between the counterclockwise or upstream end of the recess 55 and the clockwise or downstream end of the recess 54. In this way, an efficient rinsing of the measuring passageway 35 is ensured, the width of the recesses 54, 55 ensuring that the areas of the valve body faces adjacent to the ends of the measuring passageway 35 are also rinsed.

Certain further features of the illustrated apparatus have been omitted from FIGS. 1 and 2A, 2B to simplify the illustration. These features are explained below with reference to the description of the operation of the apparatus, and to some extent they are also shown in FIGS. 3 to 8.

When a liquid sample, e.g. a blood sample, is to be serially diluted by means of the illustrated apparatus, the valve body 23 is first rotated to the position shown in FIGS. 1 and 3. A portion of the undiluted blood sample is then drawn from a sample tube by the pump 13 so that the measuring passageway 35 is completely filled. A measured volume of the sample, that is, the volume of the sample contained in the passageway 35, is then isolated from the remainder of the sample by rotating the valve body 23 counterclockwise.

After the valve body 23 has been rotated until the passageway 35 is in register with the ports 49 and 51, see FIG. 4, the pump 15 is actuated to discharge a measured volume of diluent. Initially, the diluent displaces the isolated volume of the sample contained in the passageway 35 into the mixing vessel 33 in which the sample and the diluent are intimately intermixed by the stirrer 32. Increase of the pressure in the mixing vessel 33 as a consequence of the supply of liquid is prevented because the valve body 23 keeps a vent passage open. This vent passage is formed by a passage 60 in the bottom plate 22 and a recess 63 in the valve body 23.

Upon further counterclockwise rotation, the valve body 23 reaches a position in which the passageway 35 is in register with the recesses 54, 55, any residues of the sample still left in the passageway 35 being rinsed away by the wash liquid. At the same time, the faces of the valve body 23 are rinsed within a region around the ends of the passageway 35. This operation is shown in FIG. 5.

After the passageway 35 has been moved beyond the counterclockwise end of the recesses 54 and 55, the rinsing of the annular area of each end face of the valve body 23 in which the adjacent end of the passageway 35 is located is continued, see FIG. 6. The resistance to flow in the flow path between the counterclockwise end of the recess 55 and the clockwise end of the recess 54 now is substantially greater than in the position shown in FIG. 5, because there is no short-circuiting by the passageway 35. If sample residues moving with the valve body 23 should remain within the just-mentioned area, such residues can also be rinsed away.

In the valve body position shown in FIG. 7, the rotation of the valve body has progressed sufficiently to place the passageway 35 in register with the ports 40, 42. In this position the pump 13 draws a small portion of the once diluted sample solution present in the mixing vessel 33 so that the passageway 35 is filled with that solution.

When the valve body 23 has been rotated to the position shown in FIG. 8, in which the passageway 35 with the isolated diluted sample solution is in register with the ports 43, 46, the pump 15 is again actuated to discharge a measured volume of diluent and the isolated volume of the once diluted sample solution in the passageway 35 through the conduit 44 into the receiving vessel 45.

At the same time, the interior of the mixing vessel 33 is pressurized by an air pump 61 which is connected to the vent passage 60 (FIG. 8) so that the once diluted sample solution in the mixing vessel 33 is discharged through the transfer conduit 52 into the receptacle 53.

In the illustrated embodiment the piston pump 15 discharges equal volumes of diluent, many times larger than the volume contained in the passageway 35, in the positions shown in FIGS. 4 and 8. The discharge volume is adjusted such that the twice diluted solution in the receiving vessel 45 has the desired concentration. If then, as is normally the case, the once diluted solution transferred from the mixing vessel 33 to the receptacle 53 is insufficiently diluted, the requisite additional amount of diluent is added in the receptacle 53. The normally required agent for hemolyzing red blood cells may be included in or constitute such additional diluent and is supplied by means of the piston pump 16 from a container 62.

Alternatively, the diluent may be supplied by two different piston pumps, the volumes discharged by the pumps being selected to produce the desired final concentrations without further dilution. Naturally, it is also possible to use a single pump discharging different volumes of diluent in a single dilution cycle.

It should be understood that variations in the construction of the valve device of the invention may be made without departing from the scope of the invention as claimed.

What I claim is:

1. A valve device for use in apparatus for serial dilution of liquid samples, comprising:
   (a) a valve housing having a sample inlet connectable to a source of liquid sample, a diluent inlet connectable to a source of liquid diluent, a third inlet and a first outlet, both being connectable to a first sample recipient, a second outlet connectable to a second sample recipient, pairs of first and second pump connection ports connectable to pump means for conveying liquid sample and diluent within said valve device, said pair of second pump connection ports forming said diluent inlet;
   (b) a valve body mounted in said housing for movement therein and having a passageway of predetermined volume opening into opposite surfaces of said valve body, said passageway in a first valve body position connecting said sample inlet with one of said pair of first pump connection ports, in a second valve body position connecting one of said pair of second pump connection ports with said first outlet, in a third valve body position connecting said third inlet with the other of said pair of first pump connection ports, and in a fourth valve body position connecting the other of said pair of second pump connection ports with the second outlet; and
   (c) a valve body actuator for selectively moving said valve body relative to said housing into one of said aforementioned valve body positions;
   (d) said housing having recesses which are open towards said opposite valve body surfaces and in register with the path along which the ends of said passageway move during movement of said valve body between said second and third valve body positions, said recesses being connectable with a wash liquid conveying system and in at least one valve body position between said second and third valve body positions communicating simeultaneously with said passageway.

2. A valve device as claimed in claim 1, each said recess being elongated and extending along said path over a major portion of the space separating said second and third valve body positions, the width of said recesses being larger than the width of the respective adjacent end of said passageway.

3. A valve device as claimed in claim 2, opposite ends of each recess having respectively an outlet and an inlet for wash liquid.

4. A valve device according to claim 2 for use in an apparatus, each said recess having spaced inlet and outlet ends, the inlet end of one of the recesses being connected to a wash liquid inlet, means fluidly interconnecting the outlet end of said one recess with the inlet end of the other recess, the outlet end of said other recess being connected to a wash liquid outlet, and the resistance to fluid flow of the flow path formed by the recesses and the fluid flow connection between said outlet end of said one recess and said inlet end of said other recess being substantially greater than the resistance to fluid flow of the flow path which, with the ends of said passageway registering with said recesses, is formed by the portion of said one recess situated between said inlet end of said one recess and said passageway, said passageway, and the portion of said other recess situated between said passageway and said outlet end of said other recess.

* * * * *